United States Patent
Kobayashi et al.

(10) Patent No.: US 7,376,452 B2
(45) Date of Patent: May 20, 2008

(54) APPARATUS AND METHOD FOR MEASURING TRANSIT TIME OF OXYGEN IN BLOOD

(75) Inventors: Naoki Kobayashi, Tokyo (JP); Hiroshi Kubota, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 11/341,421

(22) Filed: Jan. 30, 2006

(65) Prior Publication Data
US 2006/0173258 A1 Aug. 3, 2006

(30) Foreign Application Priority Data
Jan. 28, 2005 (JP) ............................. P2005-021087
Mar. 30, 2005 (JP) ............................. P2005-097080

(51) Int. Cl.
*A61B 5/00* (2006.01)
(52) U.S. Cl. ...................... 600/322; 600/323
(58) Field of Classification Search ............... 600/322, 600/323, 324
See application file for complete search history.

(56) References Cited

U.S. PATENT DOCUMENTS

| | | | |
|---|---|---|---|
| 4,223,680 A | 9/1980 | Joebsis et al. | |
| 5,251,632 A * | 10/1993 | Delpy | 600/323 |
| 5,810,723 A | 9/1998 | Aldrich | |
| 6,334,065 B1 * | 12/2001 | Al-Ali et al. | 600/323 |
| 6,355,000 B1 | 3/2002 | Ogura | |
| 6,565,515 B2 | 5/2003 | Ogura | |
| 6,577,884 B1 | 6/2003 | Boas | |
| 2002/0091328 A1 | 7/2002 | Ogura | |
| 2003/0109772 A1 | 6/2003 | Mills | |

FOREIGN PATENT DOCUMENTS

| | | |
|---|---|---|
| EP | 0 502 270 A1 | 9/1992 |
| JP | 3028152 B2 | 2/2000 |
| JP | 2000-107157 A | 4/2000 |

* cited by examiner

*Primary Examiner*—Eric Winakur
*Assistant Examiner*—Etsub D Berhanu
(74) *Attorney, Agent, or Firm*—Sughrue Mion, PLLC

(57) ABSTRACT

In order to measure a transit time of oxygen in blood, at least one sensor is attached to at least one prescribed position on a subject. The sensor is adapted to detect a light absorption of arterial blood at the prescribed position. An oxygen saturation of the arterial blood at the prescribed position is calculated based on the detected light absorption. An amount of oxygen inspired into the subject is varied at a reference time point. A change in the calculated oxygen saturation at the prescribed position is detected. A time period from the reference time point to a time point at which the oxygen saturation changes is measured.

15 Claims, 11 Drawing Sheets

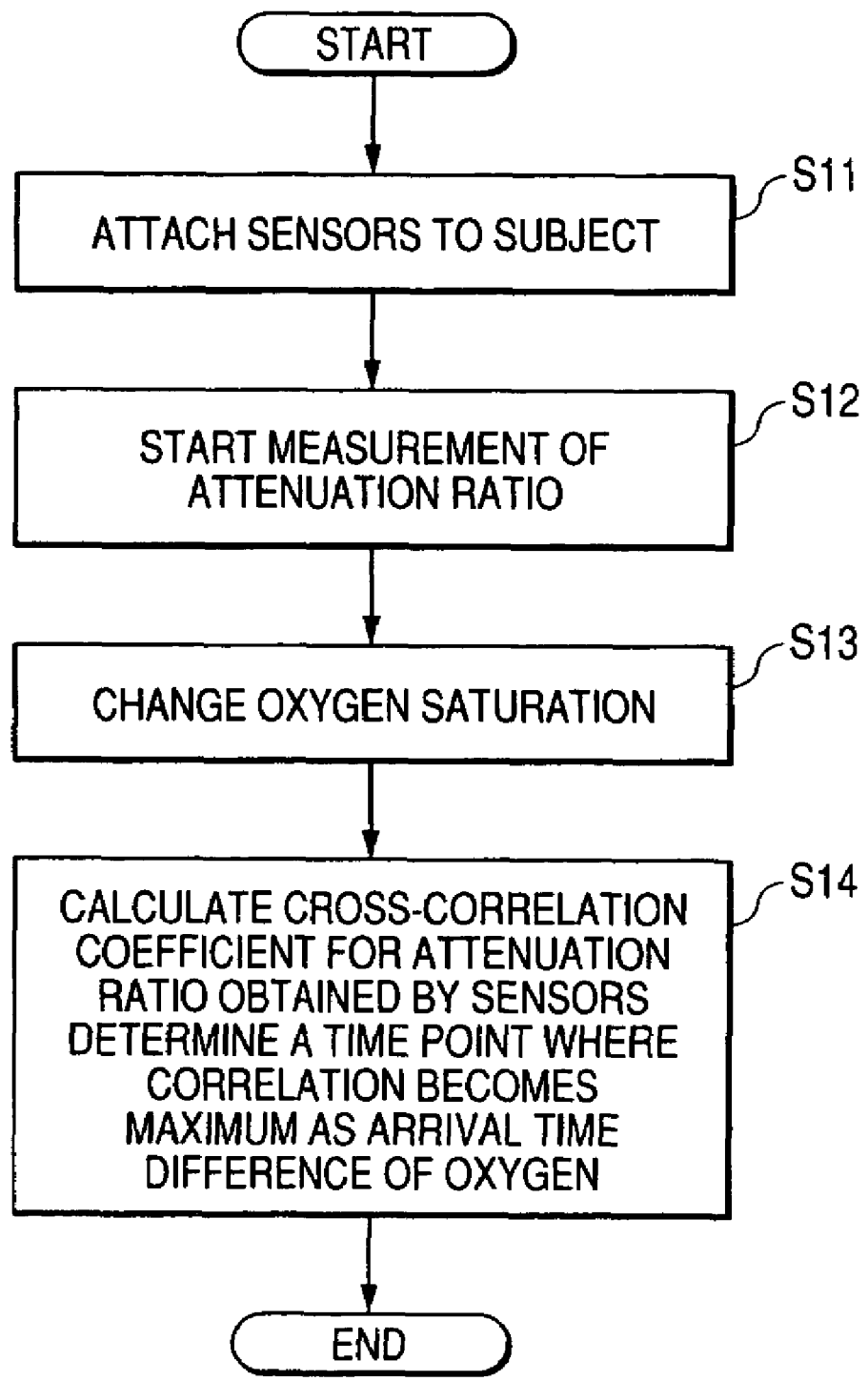

NASAL WING
TRANSIT TIME : 30 sec

FINGERTIP
TRANSIT TIME : 160 sec

APPARATUS AND METHOD FOR MEASURING TRANSIT TIME OF OXYGEN IN BLOOD

BACKGROUND OF THE INVENTION

The present invention relates to an apparatus and a method for measuring a transit time of oxygen in blood, which serves as an index of an ability of blood flow for delivering oxygen (transit time of oxygen) with regard to various organs in a living body, as a change in an oxygen concentration in blood with a non-invasive manner.

Conventionally, a cardiac output has been an important parameter serving as an index of an oxygen conveying ability to various organs in a living body. For measurement of the cardiac output, a method of inserting a catheter to the heart, thereby measuring the cardiac output in accordance with a thermodilution method, is generally known. However, since cold water must be injected into the living body, the thermodilution method involves a problem of significant invasion of the living body, and is expensive as well.

For example, Japanese Patent No. 3028152 discloses a cardiac output measuring device for measuring a cardiac output by injecting dye into a vein of a living body. More specifically, the cardiac output measuring device is configured so as to obtain a cardiac output by the following procedure. A prescribed amount of dye is injected into a vein at a portion of a living body; and the dye, which has arrived at an artery at another portion of the living body, is detected. A time Ta (a mean transit time) denoting a time elapsed between completion of the dye injection and a start of detection of the arrived dye, and a time Tp denoting a time elapsed before the detected dye concentration reaches its peak concentration are measured, thereby attaining measurement of a cardiac output.

As illustrated in FIGS. 12A and 12B, the mean transit time of blood flow is known to be a parameter having good correlation with cardiac output. More specifically, FIG. 12A shows a relationship between the mean transit time (sec) and a cardiac index (1 /min/m$^2$); and FIG. 12B shows a relationship between corrected mean transit time (sec/M) corrected by a height (M) and a cardiac index (1 /min/m$^2$). As is apparent from these relationships, the mean transit time is proportional to the cardiac index. Therefore, the mean transit time of the blood flow can be employed as a parameter serving as an index of circulation of the blood flow, as in the case of cardiac output. Meanwhile, the transit time and the cardiac output have a good correlation in spite of being independent parameters of different dimensions. Accordingly, one can expect that, when the transit time of the blood flow can be measured easily, non-invasively, continuously, and at low cost, from a medical viewpoint the transit time can serve as a useful parameter for circulation monitoring in lieu of the cardiac output.

In addition, the above-mentioned measurement of the transit time of the blood flow serves as an index of not only cardiac output, but also of the peripheral circulation of the blood flow. For instance, FIGS. 13A and 13B show results of measurement in a case where sensors are attached to a nasal wing and to a fingertip of a subject whose peripheral blood vessel is constricted after cardiac surgery, in which arrival times of ICG (indocyanine green) at the sensors are measured simultaneously in accordance with the above dye dilution method.

More specifically, as shown in FIG. 13A, a mean transit time from injection of dye into the right atrium to arrival of the same at the nasal wing is about 30 seconds. Meanwhile, as shown in FIG. 13B, a mean transit time elapsed before arrival at the fingertip is about 160 seconds. As described above, a transit time to a fingertip is dominated by a time elapsed before arrival at the fingertip from the aorta, and this sometimes takes a significantly long time during a period of constriction of the peripheral blood vessel. Accordingly, as is apparent, when a blood vessel is clogged due to arteriosclerosis, or the like, the blood flow is reduced, thereby delaying the transit time thereof. However, the above measurement method of injecting dye into a vessel for measuring such a transit time involves a problem of requiring invasion of a living tissue, as well as being unable to carrying out continuous measurement.

On the other hand, low-invasive measurement methods that have been put into practice include a pulse dye dilution method, an impedance method, a transesophageal ultrasonic Doppler method, and a $CO_2$ Fick method However, the pulse dye dilution method has a problem of requiring injection of dye into a vein, and being unable to carrying out continuous measurement. The impedance method has a problem of deteriorated accuracy when a subject is connected with a variety of electrodes and/or infusion lines. The transesophageal ultrasonic Doppler method requires insertion of an esophageal probe, thereby involving a problem of allowing measurement only under anesthesia. Measurement in accordance with the $CO_2$ Fick method can be made only with an intubated patient, thereby posing a problem of deteriorated accuracy during a period that the cardiac output is changing.

SUMMARY OF THE INVENTION

It is therefore an object of the invention to provide an apparatus and a method for measuring a transit time of oxygen in blood, capable of readily and continuously measuring a transit time of blood flow as a bioparameter, which serves as an index for determination of an ability of blood flow for delivering oxygen (transit time of oxygen) to various organs in a living body, as a change in an oxygen concentration in blood with a non-invasive manner, and at low cost.

In order to achieve the above object, according to the invention, there is provided a method for measuring a transit time of oxygen in blood, comprising:

attaching at least one sensor to at least one prescribed position on a subject, the sensor being adapted to detect a light absorption of arterial blood at the prescribed position;

calculating an oxygen saturation of the arterial blood at the prescribed position, based on the detected light absorption;

varying an amount of oxygen inspired into the subject at a reference time point;

detecting a change in the calculated oxygen saturation at the prescribed position; and measuring a time period from the reference time point to a time point at which the oxygen saturation changes.

The inspired amount of oxygen may be varied by causing the subject to perform at least one of a deep breathing and a breath hold.

The inspired amount of oxygen may be varied by varying a concentration of oxygen to be inspired.

The oxygen saturation may be obtained by a pulse oximeter.

A plurality of sensors may be attached to a plurality of prescribed positions on the subject. In this case, each of the sensors is adapted to detect the light absorption at each of the prescribed positions. The oxygen saturation is calculated at each of the prescribed positions, based on the light absorption detected by each of the sensors. The change in the calculated oxygen saturation is detected at each of the prescribed positions. The time period is measured for each of the prescribed positions.

The measuring method may further comprise determining a difference between time periods measured at prescribed positions.

The measuring method may further comprise:

obtaining a cross-correlation coefficient between attenuation rates or oxygen saturations measured by the sensors; and determining the difference based on a time period from the reference time point to a time point at which the cross-correlation coefficient becomes maximum.

According to the invention, there is also provided an apparatus for measuring a transit time of oxygen in blood, comprising:

at least one sensor, adapted to be attached to at least one prescribed position on a subject, the sensor being operable to detect a light absorption of arterial blood at the prescribed position;

a first calculator, adapted to calculate an oxygen saturation of the arterial blood at the prescribed position, based on the detected light absorption;

a first detector, adapted to detect a first time point at which an amount of oxygen inspired into the subject is varied; and a second detector, adapted to detect a second time point at which the calculated oxygen saturation changes to determine a time period from the first time point to the second time point.

The first detector may be a flow sensor adapted to detect that the inspired amount of oxygen is varied.

The measuring apparatus may further comprise a valve operable to vary a concentration of oxygen to be inspired.

The oxygen saturation may be obtained by a pulse oximeter.

A plurality of sensors may be attached to a plurality of prescribed positions on the subject. In this case, each of the sensors is adapted to detect the light absorption at each of the prescribed positions. The oxygen saturation is calculated at each of the prescribed positions, based on the light absorption detected by each of the sensors. The change in the calculated oxygen saturation is detected at each of the prescribed positions. The time period is measured for each of the prescribed positions.

The measuring apparatus may further comprise a second calculator, operable to determine a difference between time periods measured at prescribed positions.

The measuring apparatus may further comprise a third calculator, operable to obtain a cross-correlation coefficient between attenuation rates or oxygen saturations measured by the sensors. The difference may be determined based on a time period from the reference time point to a time point at which the cross-correlation coefficient becomes maximum.

When an amount of inspired oxygen is caused to change through a fractional concentration of oxygen in inspired gas $FIO_2$, the arterial oxygen saturation $SpO_2$ changes. Currently, the arterial oxygen saturation $SpO_2$ can generally be readily measured by a pulse oximeter. When the $FIO_2$ is taken as an input, and arterial oxygen saturation $SpO_2$ is taken as an output, a positive correlation is found between the input and the output. More specifically, at a high $FIO_2$, the arterial oxygen saturation $SpO_2$ is high; and at a low $FIO_2$, the arterial oxygen saturation $SpO_2$ is low. When, for instance, a stepwise signal (of $FIO_2$) is input, a response signal (of arterial oxygen saturation $SpO_2$) including a certain delay time is output. By measuring this delay time, there can be obtained a transit time of oxygen through: oxygen inhalation→the lung→the heart→the aorta→the peripheral measurement positions.

A condition of oxygen delivery to each of the prescribed positions can be ascertained on the basis of oxygen concentrations in blood obtained with use of the sensors. For instance, when, as a result of measurement of a transit time of the blood flow in right and left lower limbs, the transit time of one side is found to be long, reduction of blood flow can be detected. Hence, cases where blood flow is deteriorated by development of thrombus or atheroma can also be detected on the basis of the transit time.

BRIEF DESCRIPTION OF THE DRAWINGS

The above objects and advantages of the present invention will become more apparent by describing in detail preferred exemplary embodiments thereof with reference to the accompanying drawings, wherein:

FIG. 5 is a flowchart illustrating a measurement performed in the measuring apparatus of FIG. 4;

DETAILED DESCRIPTION OF THE EMBODIMENTS

Embodiments of the invention will be described in detail with reference to the accompanying drawings.

Figure 1:
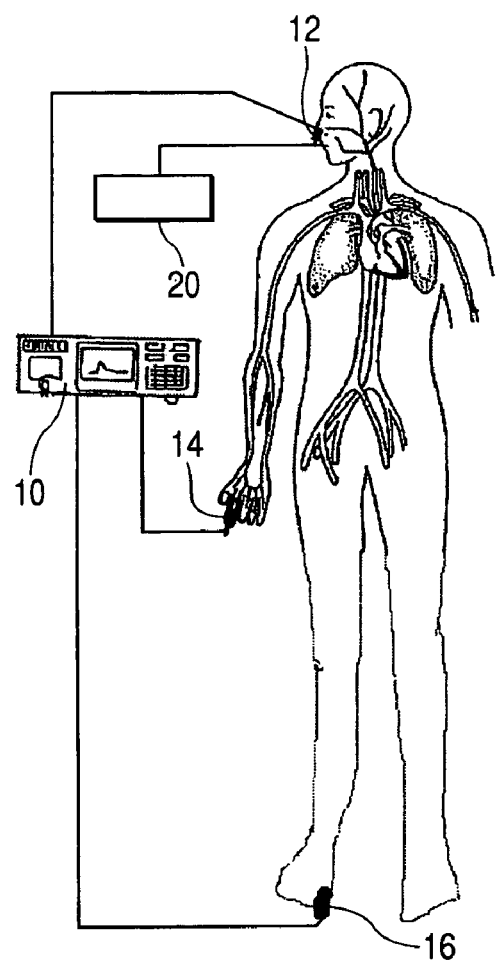
FIG. 1 is a schematic view for explaining how to measure a transit time of oxygen in blood according to the invention.

In FIG. 1, reference numeral 10 denotes a pulse oximeter for measuring arterial oxygen saturation $SpO_2$ at a plurality of prescribed positions of a living body. The apparatus includes light absorption sensors which are to be connected to the pulse oximeter 10, and which are constituted of a first sensor 12 disposed on a nasal wing; a second sensor 14 disposed on a fingertip; and a third sensor 16 disposed on a toe, each of which belongs to the living body. In addition, an oxygen cylinder 20 is disposed in a mouth of the living body.

Meanwhile, for measurement of the arterial oxygen saturation $SpO_2$, the sensors are configured as follows. Each of the sensors has a photo emitter and a photo detector, and is configured to sandwich a measurement position of the living body therebetween. Two light-emitting diodes, having light-emitting wavelengths of 660 nm and 940 nm, are used as the photo emitter. The light-emitting diodes are set so as to emit light alternately. A photo diode is used as the photo detector. Thus, light is emitted from the photo emitter, passes through the measurement position of the living body, and arrives at the photo detector. The intensity of the thus-arrived light is converted into current by the photo diode; is further converted into voltage in the pulse oximeter; and is separated into transmitted-light signals of the respective wavelengths. Thereafter, pulse wave components of the light absorption are extracted from the two transmitted-light signals. A ratio of amplitudes of the pulse wave components; that is, an attenuation ratio Φ is calculated; and the ratio is converted into oxygen saturation, thereby obtaining arterial oxygen saturation $SpO_2$.

Figure 2:
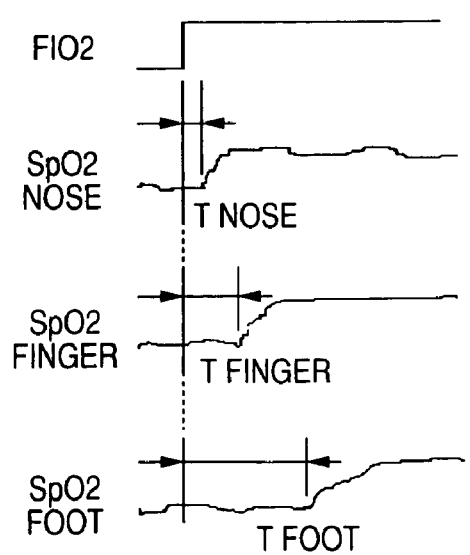
FIGS. 2 and 3 are waveform diagrams for explaining how to measure a transit time of oxygen in blood according to the invention.

FIG. 2 illustrates change with time of the attenuation ratios Φ or the arterial oxygen saturation $SpO_2$ in a case where, e.g., the fractional concentration of oxygen in inspired gas $FIO_2$ is changed by causing oxygen to be inhaled with use of the oxygen cylinder 20 in measurement of arterial oxygen saturation $SpO_2$ at the respective positions of the living body in the system configuration illustrated in FIG. 1. The attenuation ratios Φ or the arterial oxygen saturation $SpO_2$ are detected and measured by the first through third sensors 12, 14, and 16 disposed at the respective positions of the living body.

Figure 3:
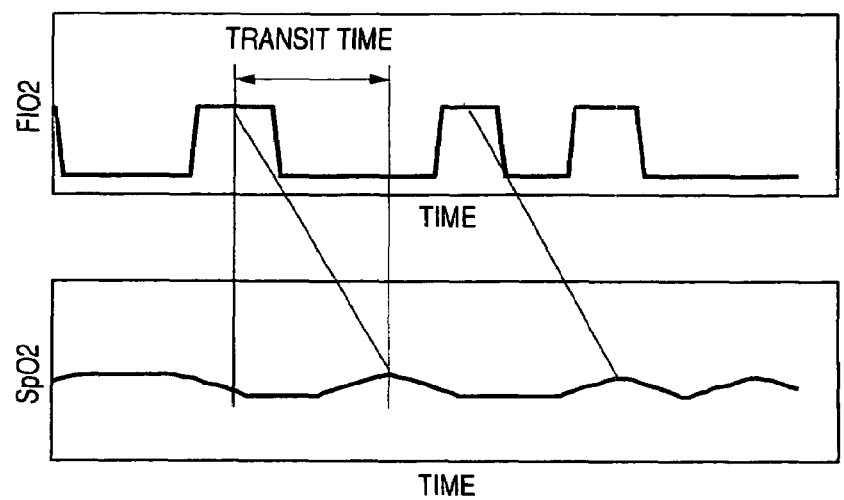

More specifically, as is apparent in FIG. 2, a time Tnose, Tfinger, Tfoot elapsed between a point in time when the $FIO_2$ of the living body is caused to change and a point in time when the arterial oxygen saturation $SpO_2$nose, $SpO_2$finger, $SpO_2$foot increases at each of the measurement positions; that is, a transit time during which oxygen is transported along the blood flow, can be determined. In this case, the rising edges of the arterial oxygen saturation appear in the nasal wing, the fingertip of a hand, and the toe, in this order. In particular, since the blood flow in the head is maintained even in a situation where the peripheral blood vessels such as those in the hands and feet are contracted and the blood flow is reduced, the transit time in the nasal wing (head) exhibits good correlation with cardiac output. By changing the $FIO_2$ so as to form rectangular waves as shown in FIG. 3, continuous determination of the transit time can be attained.

Figure 4:
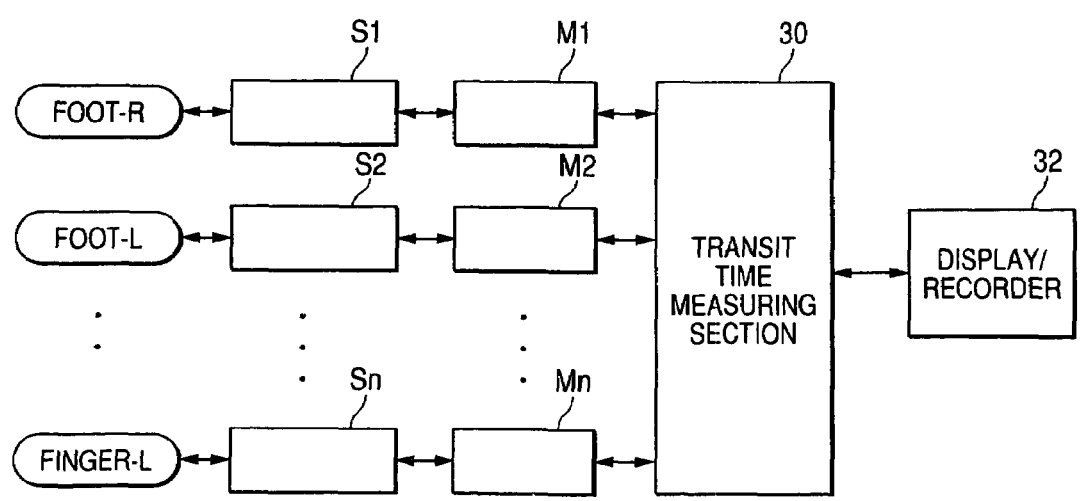
FIG. 4 is block diagram illustrating a measuring apparatus according to a first embodiment of the invention.

FIG. 4 shows a measuring apparatus according to a first embodiment of the invention. Light absorption sensors S1, S2, . . . Sn and measuring sections M1, M2, . . . Mn for obtaining the attenuation ratios Φ or the arterial oxygen saturation $SpO_2$ are respectively connected to measurement positions constituted of a toe of the right foot "Foot-R" of a subject, a left toe "Foot-L," and a finger of the left hand "Finger-L." Furthermore, a transit time measuring section 30 and a display (recorder) 32 are respectively connected to the sensors via the respective measuring sections M1, M2, . . . Mn.

In this embodiment, as illustrated in FIG. 5, the light absorption sensors S1, S2, . . . Sn are respectively attached to the respective measurement positions of the subject (step S11), and attenuation ratios Φ of the arterial blood or the arterial oxygen saturation $SpO_2$ at the respective measurement positions are measured by the respective measuring sections M1, M2, . . . Mn (step S12). Here, an amount of oxygen inspired by the subject is caused to change by deep breathing or breath-holding (step S13). Hence, the transit time measuring section 30 can calculate a difference in transit time between the respective positions on the basis of waveforms of the attenuation ratios Φ of the arterial blood or the arterial oxygen saturation $SpO_2$ at the respective the measuring sections M1, M2, . . . Mn (step S14). Meanwhile, the thus-measured difference in transit time is displayed and/or recorded in the display (recorder) 32 as required.

Figure 6A:
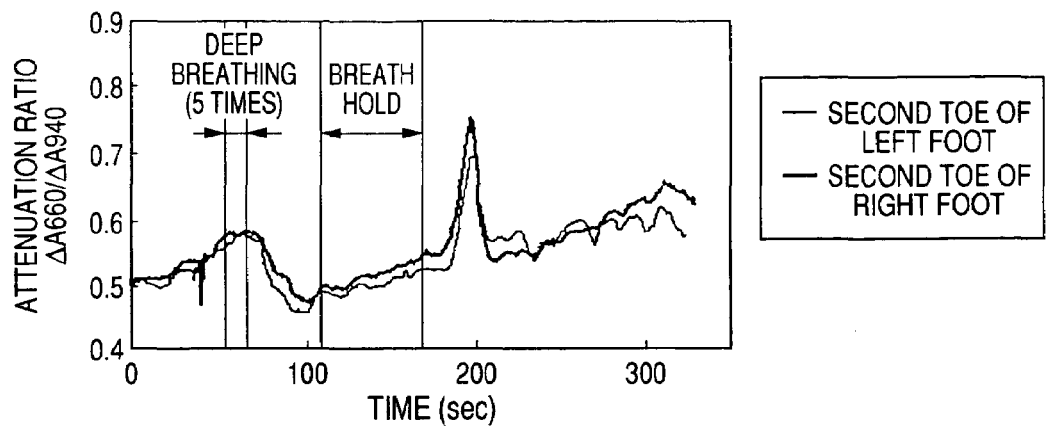
FIGS. 6A and 6B are graphs each showing change with time of arterial oxygen saturation measured by the measuring apparatus of FIG. 4.
Figure 6B:
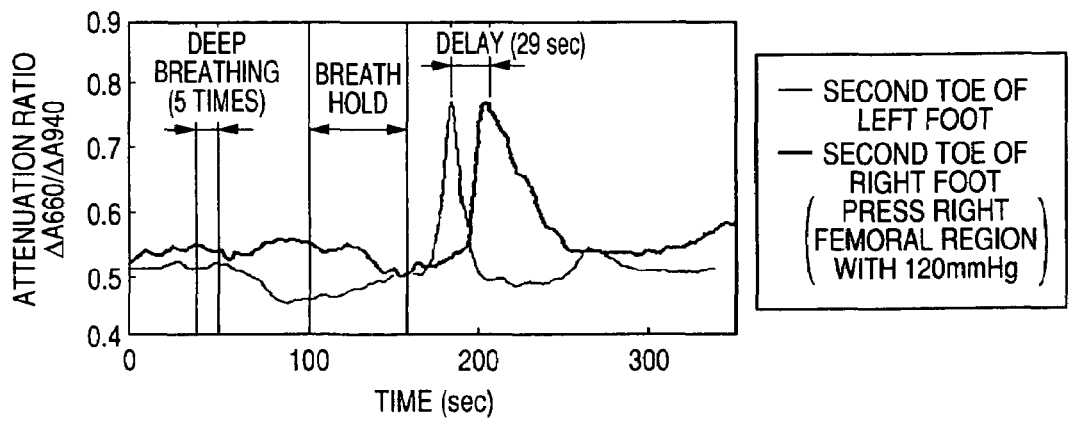

FIG. 6A shows a result of measurement, measured by the transit time measuring apparatus of the present embodiment, of the attenuation ratio Φ of the arterial blood at the right toe "Foot-R" and that of the left toe "Foot-L" of a subject in a case where the subject performs deep breathing five times, and thereafter maintains a predetermined breath-holding state. FIG. 6B shows a result of the same measurement as above in a case where a right femoral region of the subject is pressed with a pressure of 120 mmHg.

Figure 6C:
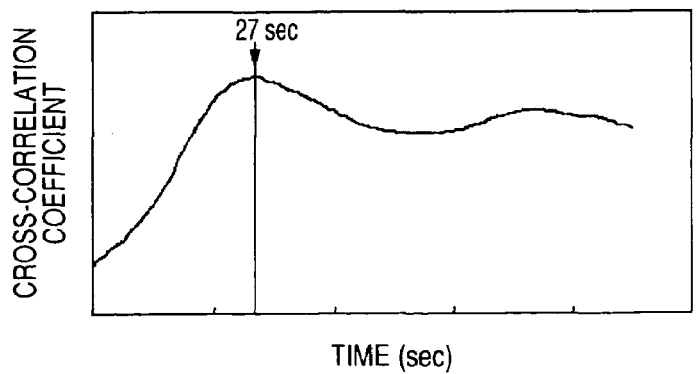
FIG. 6C is a graph showing a cross-correlation coefficient between two waveforms shown in FIG. 6B.

According to the results of the measurements, when a difference in transit time is taken at points in time when the maximum values are respectively indicated, the transit time pertaining to the right foot has a delay (29 seconds). Hence, an abnormality with regard to the blood vessel in the right foot can be detected. Alternatively, as another method, a difference in transit time can be taken by calculating a cross-correlation coefficient between Φ or $SpO_2$ measured at two positions, and taking a point in time when the cross-correlation coefficient attains the maximum value as the difference in transit time. FIG. 6C shows the cross-correlation coefficient between two waveforms shown in FIG. 6B.

Figure 7:
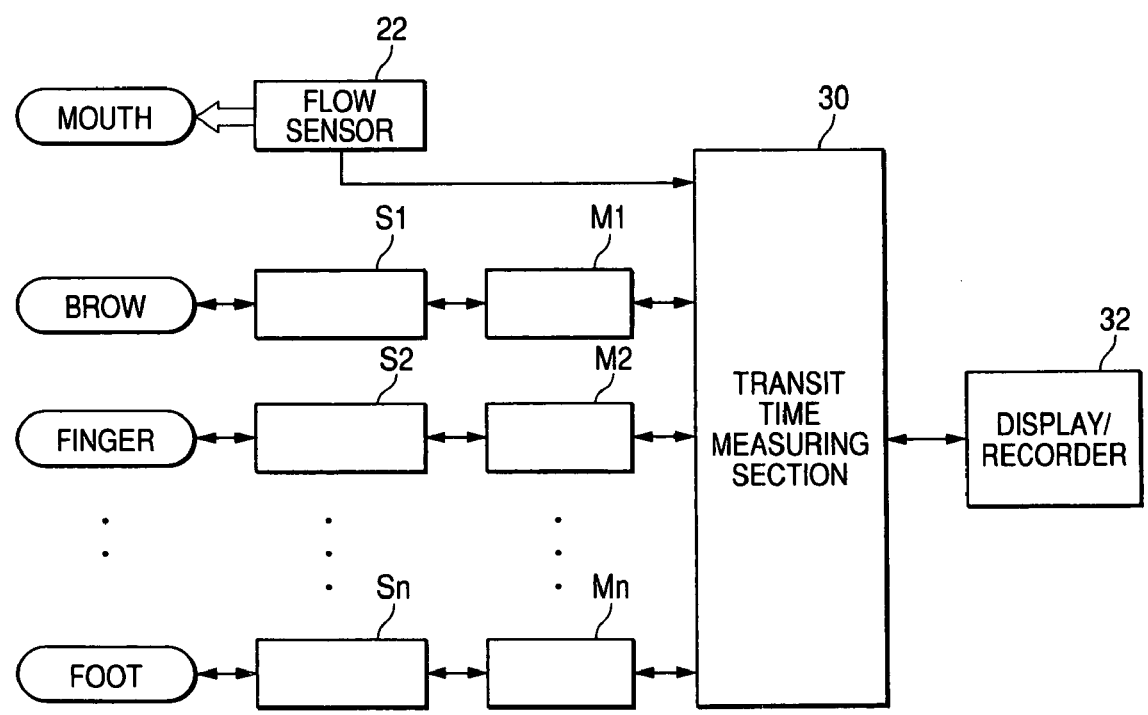
FIG. 7 is block diagram illustrating a measuring apparatus according to a second embodiment of the invention.

FIG. 7 shows a measuring apparatus according to a second embodiment of the invention. Components similar to those in the first embodiment will be designated by the same reference characters and repetitive explanations for those will be omitted.

In this embodiment, the light absorption sensors S1, S2, . . . Sn and the measuring sections M1, M2, . . . Mn for obtaining the attenuation ratios Φ or the arterial oxygen saturation $SpO_2$ are respectively connected to measurement positions constituted of a brow, the fingertip, and the toe, each of which belongs to the living body. Furthermore, a flow sensor 22 is disposed in the mouth of the subject for measurement of a respiratory flow or a respiratory volume at the time of deep breathing or breath-holding.

Figure 8:
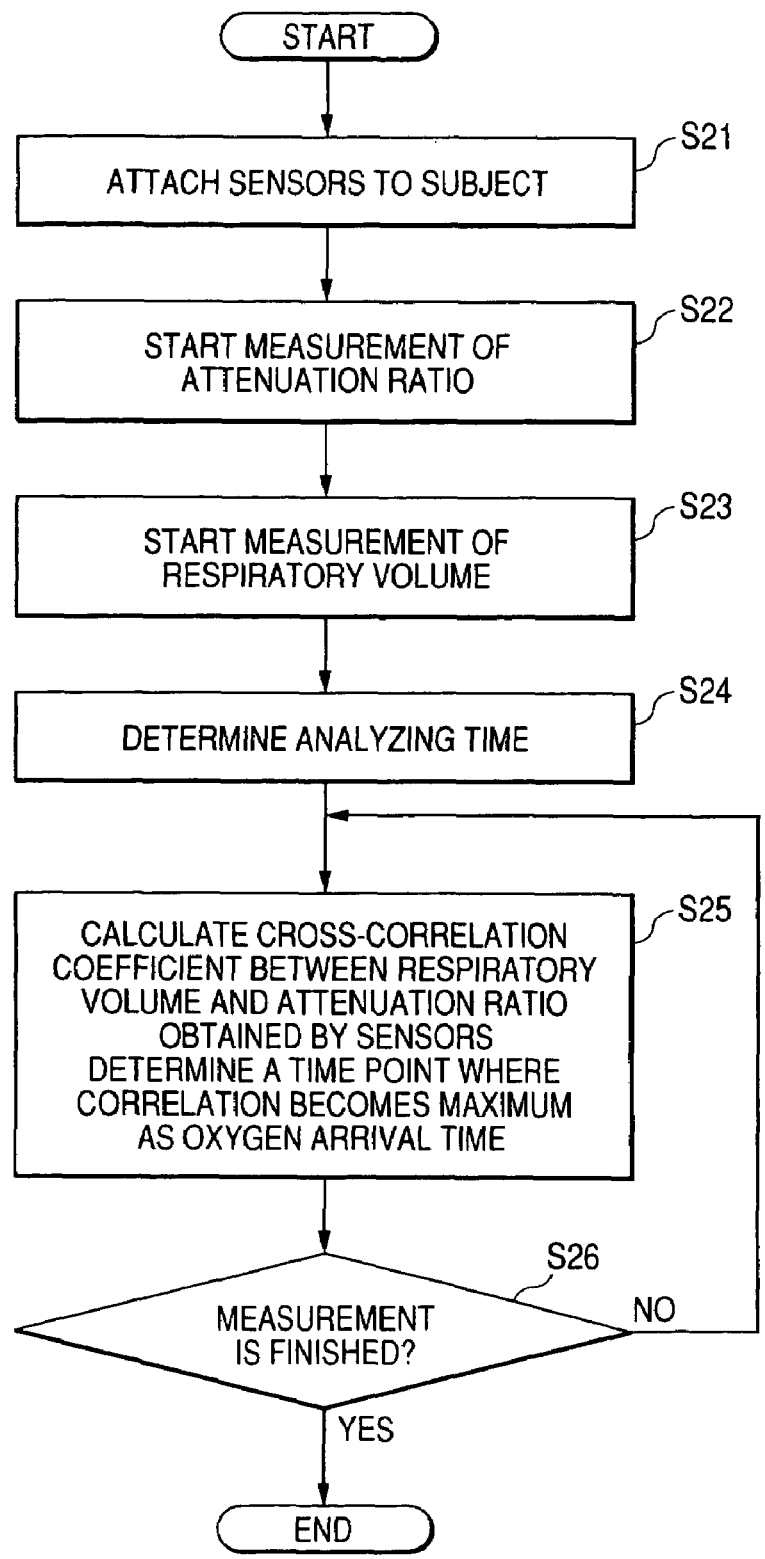
FIG. 8 is a flowchart illustrating a measurement performed in the measuring apparatus of FIG. 7.

In this embodiment, as illustrated in FIG. 8, the light absorption sensors S1, S2, . . . Sn are respectively attached to the respective measurement positions of the subject (step S21), and attenuation ratios Φ of the arterial blood or arterial oxygen saturation $SpO_2$ at the respective measurement positions are measured by the respective measuring sections M1, M2, . . . Mn (step S22). Here, the $FIO_2$ of the subject is caused to change by deep breathing or breath-holding, and, in conjunction therewith, the respiratory flow or the respiratory volume of the subject in this case is measured with use of the flow sensor 22 (step S23). Thereafter, a point in time when the $FIO_2$ is caused to change is detected.

In conjunction therewith, there is performed setting of an analysis time for measurement of a time elapsed before a change in the attenuation ratio Φ of the arterial blood or the arterial oxygen saturation $SpO_2$ to be measured by the respective measuring sections M1, M2, . . . Mn, in particular, a time elapsed before a rising edge thereof. Put another way, an analysis time for measurement of a transit time of oxygen in blood to be measured by the transit time measuring section 30 is set (step S24). In conjunction therewith, the transit time is measured within the range of the thus-set analysis time (step S25, step S26). Meanwhile, the thus-measured transit time is displayed and/or recorded on the display (recorder) 32 as required.

Accordingly, it is possible to measure a cross-correlation coefficient between the respiratory flow or the respiratory volume, and the attenuation ratios Φ of the arterial blood or the arterial oxygen saturation $SpO_2$ measured at the respective positions, so that a time when the cross-correlation coefficient attains the maximum value is taken as the transit time. Furthermore, the thus-obtained transit time serves as an index of central circulation, which has a correlation with cardiac output.

Figure 9:
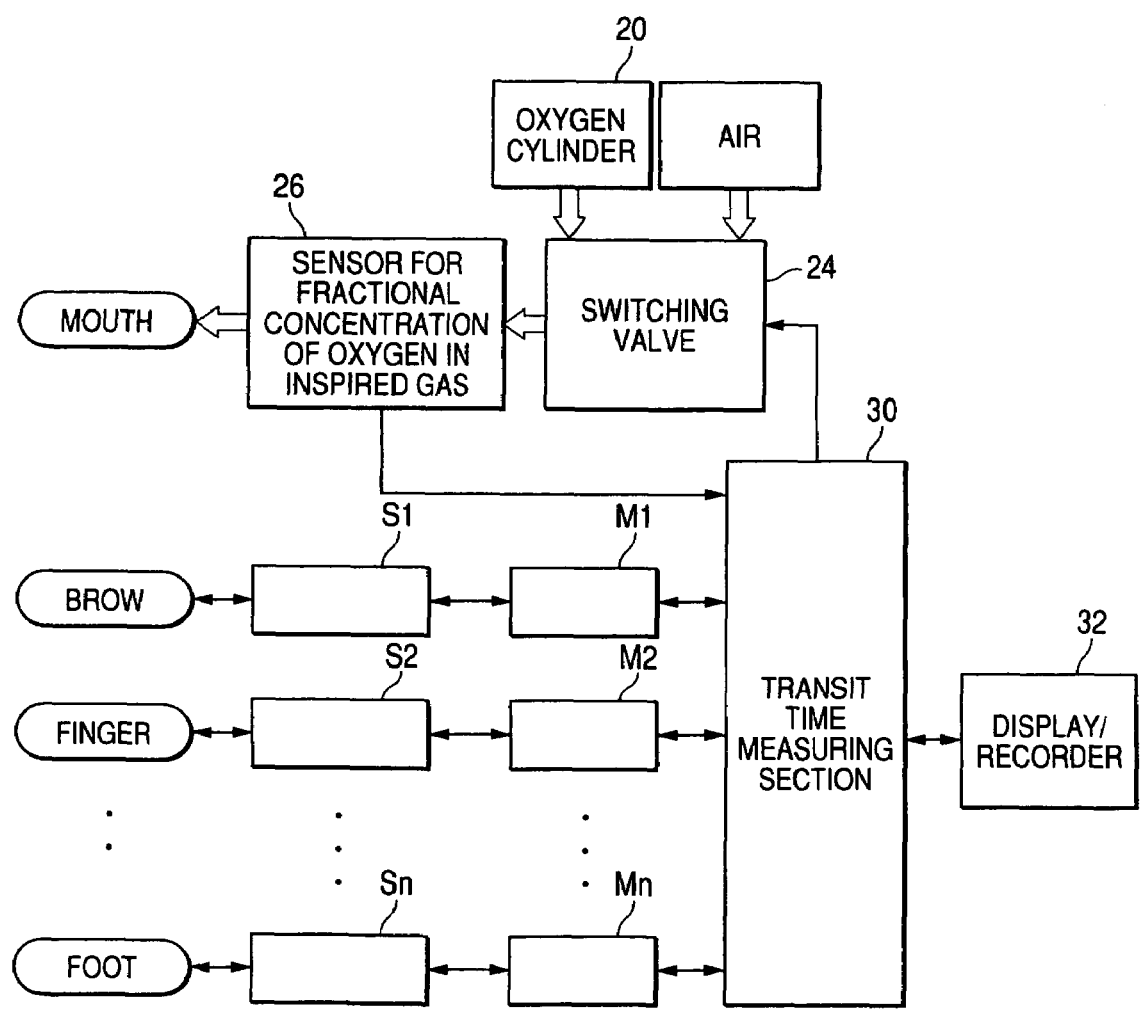
FIG. 9 is block diagram illustrating a measuring apparatus according to a third embodiment of the invention.

FIG. 9 shows a measuring apparatus according to a third embodiment of the invention. Components similar to those in the first embodiment will be designated by the same reference characters and repetitive explanations for those will be omitted.

In this embodiment, there is provided a switching valve 24 capable of adjusting a mixing ratio between oxygen gas from the oxygen cylinder 20 and the air to be supplied to the mouth of the subject. In addition, a sensor 26 for fractional concentration of oxygen in inspired gas to detect current $FIO_2$ is provided.

Figure 10:
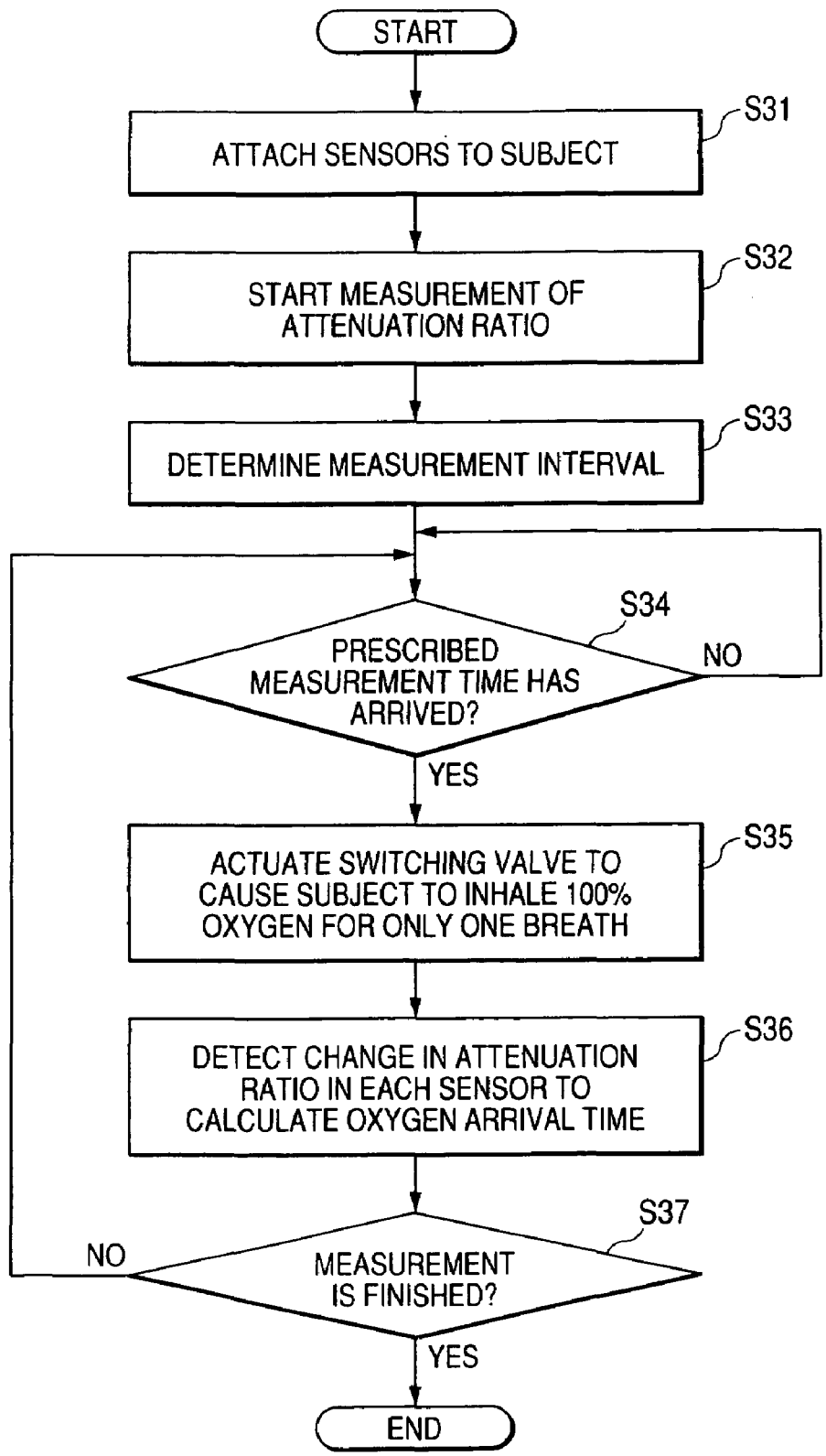
FIG. 10 is a flowchart illustrating a measurement performed in the measuring apparatus of FIG. 9.

In this embodiment, as illustrated in FIG. 10, the light absorption sensors S1, S2, ... Sn are respectively attached to the respective measurement positions of the subject (step S31), and attenuation ratios Φ of the arterial blood or arterial oxygen saturation $SpO_2$ at the respective measurement positions are measured by the respective measuring sections M1, M2, ... Mn (step S32). Here, a measurement interval for the respective measuring sections M1, M2, ... Mn is set (step S33). A determination is made as to a time for fixed-time measurement in accordance with the measurement interval having been set in advance (step S34). The switching valve 24 is switched so as to adapt to an inspiration of the subject. The subject is caused to inhale 100% oxygen for only one breath, thereby causing the $FIO_2$ to change (step S35). Thereafter, the point in time when the $FIO_2$ is caused to change is detected. In conjunction therewith, there is performed measurement of a time elapsed before a change in the attenuation ratios Φ of the arterial blood or the arterial oxygen saturation $SpO_2$ measured at the respective measuring sections M1, M2, ... Mn; in particular, a time elapsed before a rising edge. Put another way, a transit time of oxygen in blood is measured by the transit time measuring section 30 (step S36). In conjunction therewith, the transit time is measured within the range of the measurement time having been set in advance (step S37). Meanwhile, the thus-measured transit time is displayed and/or recorded in the display (recorder) 32 as required.

Figure 11A:
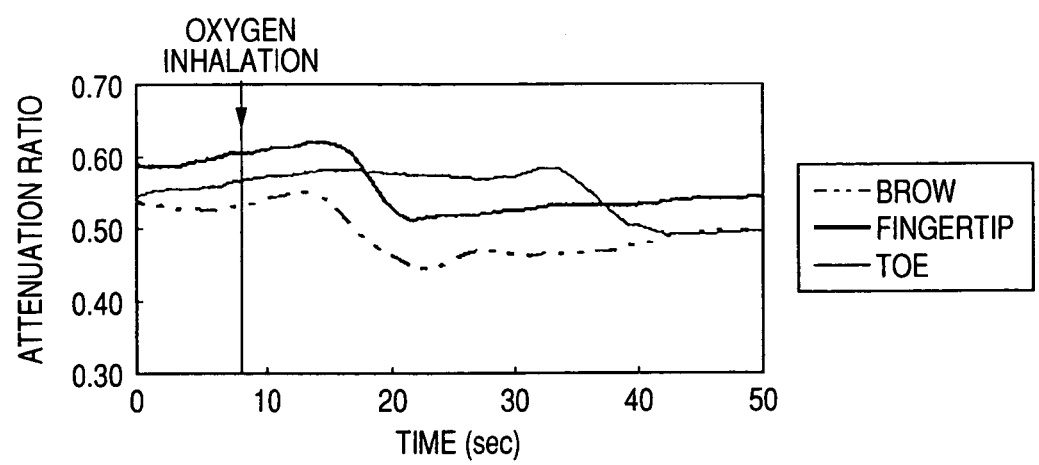
FIGS. 11A and 11B are graphs each showing changes with time of attenuation ratios respectively measured by the measuring apparatus of FIG. 9 in response to oxygen inhalation.
Figure 11B:
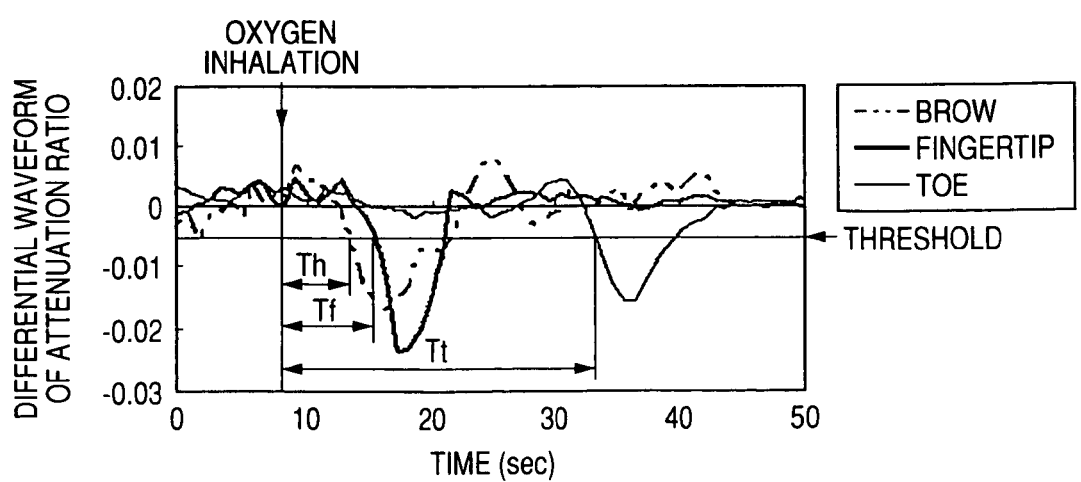
Figure 12A:
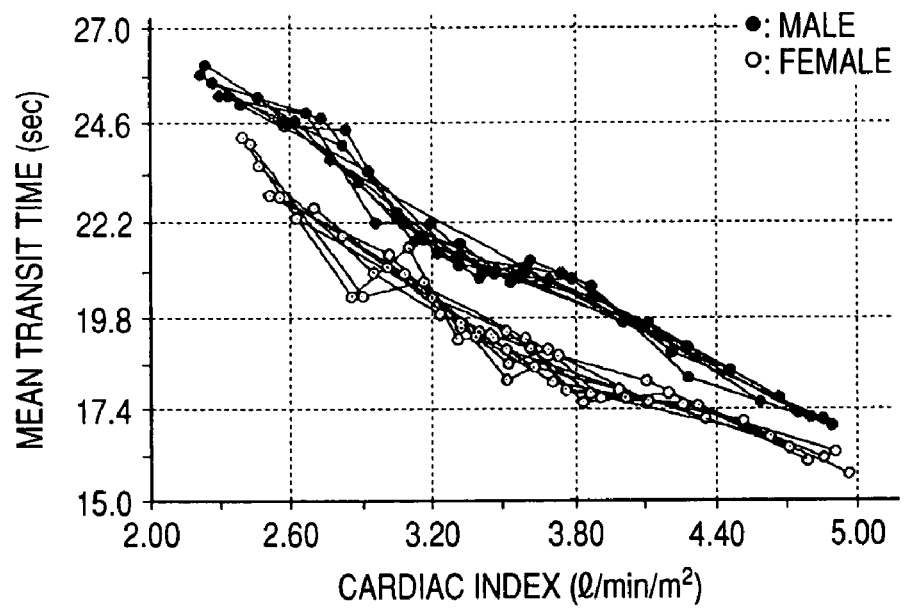
FIGS. 12A and 12B show relationships between a cardiac index and a mean transit time measured in accordance with a dye dilution method.
Figure 12B:
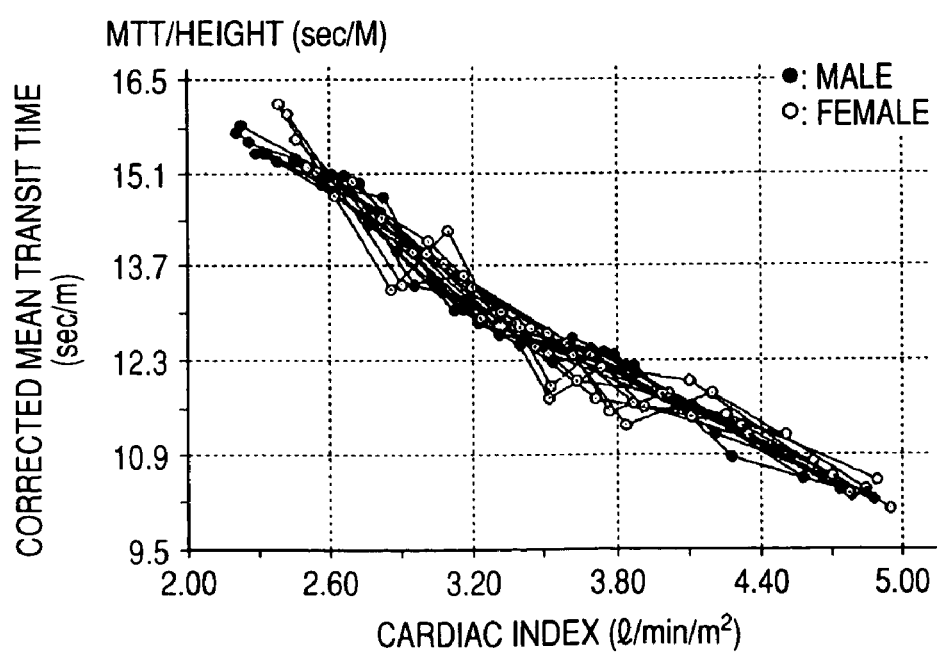
Figure 13A:
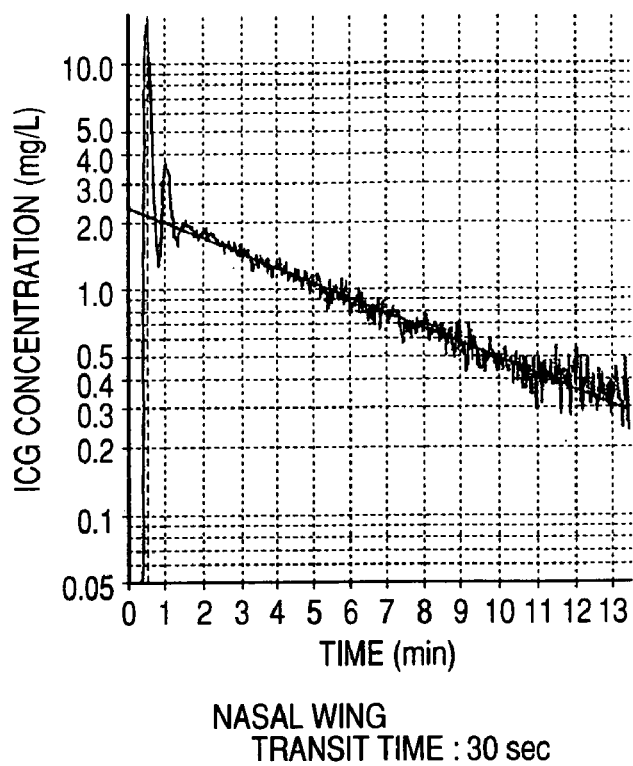
FIGS. 13A and 13B show relationship of arrival time of ICG (indocyanine green) measured in accordance with the dye dilution method.
Figure 13B:
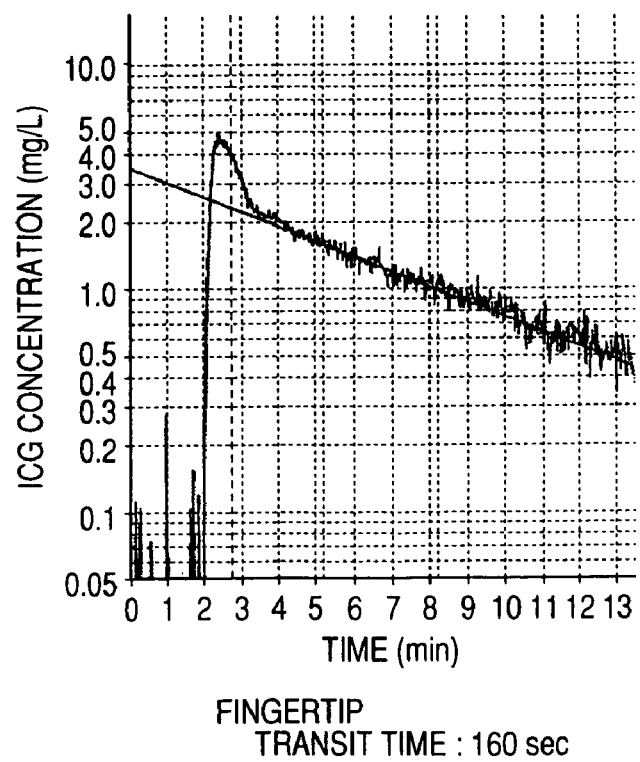

FIG. 11A shows a correlation, measured by the transit time measuring apparatus of the present embodiment, between the attenuation Φ ratio of the arterial blood at each of the measurement positions and a transit time thereof in a case where the $FIO_2$ of the subject is caused to change. FIG. 11B shows, for the sake of clarifying measurement of the transit time, a correlation between differential values in the attenuation ratios Φ of the arterial blood and the transit time, wherein the differential values are calculated with respect to a prescribed threshold value. Meanwhile, the transit time measuring apparatus of the present embodiment can perform intermittent measurement of the transit time at five-minute intervals when the $FIO_2$ of the subject is caused to change by switching inhalation of regular air to inhalation of 100% oxygen gas $O_2$ for about ten seconds at a rate of once per five minutes such that the change of the $FIO_2$ forms rectangular waves.

In this case, the switching valve 24 can be switched either automatically or manually. When the intermittent measurement is implemented, a transit time can be measured without complicating respiration management for a patient.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. A method for measuring a transit time of oxygen in blood, comprising:
   attaching a single sensor to a prescribed position on a subject, the sensor being adapted to detect a light absorption of arterial blood at the prescribed position;
   calculating an oxygen saturation of the arterial blood at the prescribed position, based on the detected light absorption;
   varying an amount of oxygen inspired into the subject at a reference time point;
   detecting a change in the calculated oxygen saturation at the prescribed position;
   measuring a time period from the reference time point to a time point at which the oxygen saturation changes; and
   outputting the measured time period as the transit time.

2. The measuring method as set forth in claim 1, wherein the inspired amount of oxygen is varied by causing the subject to perform at least one of a deep breathing and a breath hold.

3. The measuring method as set forth in claim 1, wherein the inspired amount of oxygen is varied by varying a concentration of oxygen to be inspired.

4. The measuring method as set forth in claim 1, wherein the oxygen saturation is obtained by a pulse oximeter.

5. An apparatus for measuring a transit time of oxygen in blood, comprising:
   a single sensor, adapted to be attached to a prescribed position on a subject, the sensor being operable to detect a light absorption of arterial blood at the prescribed position;
   a first calculator, operable to calculate an oxygen saturation of the arterial blood at the prescribed position, based on the detected light absorption;
   a first detector, operable to detect a first time point at which an amount of oxygen inspired into the subject is varied; and
   a second detector, operable to detect a second time point at which the calculated oxygen saturation changes to determine a time period from the first time point to the second time point.

6. The measuring apparatus as set forth in claim 5, wherein the first detector is a flow sensor adapted to detect that the inspired amount of oxygen is varied.

7. The measuring apparatus as set forth in claim 5, further comprising a valve operable to vary a concentration of oxygen to be inspired.

8. The measuring apparatus as set forth in claim 5, wherein the oxygen saturation is obtained by a pulse oximeter.

9. A method for measuring a transit time difference of oxygen in blood between prescribed positions of a subject, comprising:

attaching a plurality of sensors to the prescribed positions on the subject, each of the sensors being adapted to detect a light absorption of arterial blood at one of the prescribed positions;

calculating an oxygen saturation of the arterial blood at each of the prescribed positions, based on the detected light absorption detected by each of the sensors;

varying an amount of oxygen inspired into the subject;

detecting a change in the calculated oxygen saturation at each of the prescribed positions;

obtaining a cross-correlation coefficient between attenuation rates or oxygen saturations measured by the sensors;

determining the transit time difference, based on a time point at which the cross-correlation coefficient becomes maximum; and outputting the determined transit time difference.

10. The measuring method as set forth in claim 9, wherein the inspired amount of oxygen is varied by causing the subject to perform at least one of a deep breathing and a breath hold.

11. The measuring method as set forth in claim 9, wherein the inspired amount of oxygen is varied by varying a concentration of oxygen to be inspired.

12. An apparatus for measuring a transit time difference of oxygen in blood between prescribed positions of a subject, comprising:

a plurality of sensors, adapted to be attached to the prescribed positions on the subject, each of the sensors being operable to detect a light absorption of arterial blood at one of the prescribed positions;

a first calculator, operable to calculate an oxygen saturation of the arterial blood at each of the prescribed positions, based on the detected light absorption;

a first detector, operable to detect a change in the calculated oxygen saturation at each of the prescribed positions when an amount of oxygen inspired into the subject is varied;

a second calculator, operable to obtain a cross-correlation coefficient between attenuation rates or oxygen saturations measured by the sensors, and a third calculator, operable to determine the transit time difference based on a time point at which the cross-correlation coefficient becomes maximum.

13. The measuring apparatus as set forth in claim 12, wherein the first detector is a flow sensor adapted to detect that the inspired amount of oxygen is varied.

14. The measuring apparatus as set forth in claim 12, further comprising a valve operable to vary a concentration of oxygen to be inspired.

15. The measuring apparatus as set forth in claim 12, wherein the oxygen saturation is obtained by a pulse oximeter.

\* \* \* \* \*